US00PP34959P2

(12) United States Plant Patent
Snijder

(10) Patent No.: US PP34,959 P2
(45) Date of Patent: Jan. 31, 2023

(54) ***PELARGONIUM* PLANT NAMED 'PEQZ0094'**

(50) Latin Name: *Pelargonium*
Varietal Denomination: PEQZ0094

(71) Applicant: SYNGENTA CROP PROTECTION AG, Basel (CH)

(72) Inventor: Ronald Christiaan Snijder, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/857,207

(22) Filed: Jul. 5, 2022

(51) Int. Cl.
*A01H 5/02* (2018.01)
*A01H 6/42* (2018.01)

(52) U.S. Cl.
USPC ..... Plt./328
CPC ..... *A01H 6/425* (2018.05)

(58) Field of Classification Search
USPC ..... Plt./328
CPC ..... A01H 6/425; A01H 5/02
See application file for complete search history.

*Primary Examiner* — Keith O. Robinson
(74) *Attorney, Agent, or Firm* — Dale Skalla

(57) ABSTRACT

A new *Pelargonium* plant named 'PEQZ0094' particularly distinguished by pink colored inflorescences with semi-double florets, held above dark green foliage, on a vigorous upright, mounding plant.

1 Drawing Sheet

Figure 1:
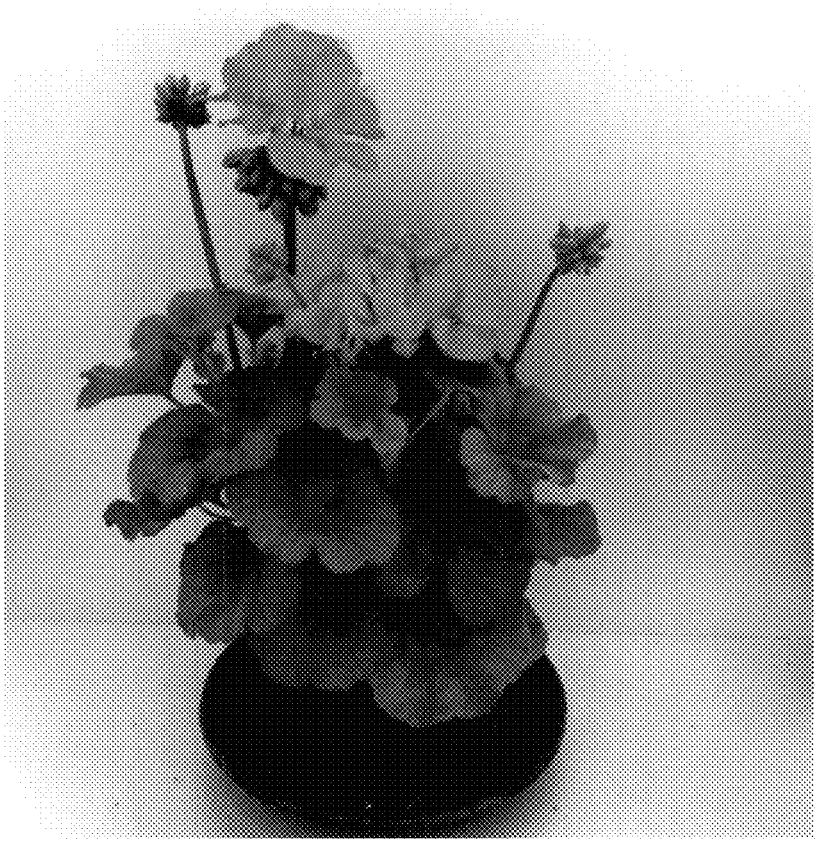

Latin name of the genus and species of the plant claimed: *Pelargonium* interspecific.

Varietal denomination: 'PEQZ0094'.

BACKGROUND OF THE NEW PLANT

The present invention comprises a new *Pelargonium*, botanically known as *Pelargonium* interspecific, and hereinafter referred to by the variety name 'PEQZ0094'.

'PEQZ0094' is a product of a planned breeding program. The new cultivar 'PEQZ0094' has large pink colored inflorescences with semi-double pink-white florets, held above dark green foliage, on a vigorous upright, mounding plant.

'PEQZ0094' originates from a hybridization in a controlled breeding program made in July 2014, in a greenhouse in Enkhuizen, The Netherlands. The female parent was a patented plant of *P.* x *hortorum* parentage 'Patriot Rose Pink' (U.S. Plant Pat. No. 18,125) with larger florets, lighter green foliage and poorer branching when compared to 'PEQZ0094'.

The male parent of 'PEQZ0094' was an unpatented, proprietary plant of *P.* x interspecific parentage, identified as 'PEI-AZ3160-01', which itself resulted from a cross between *P.* interspecific 'PEQZ0008' (U.S. Plant Pat. No. 28,423) and *P. peltatum* 'Figradol Pink' (U.S. Plant Pat. No. 20,562), with a smaller plant habit and less petals per flower when compared to 'PEQZ0094'. The resultant seed was sown in December 2014.

'PEQZ0094' was selected as one flowering plant within the progeny of the stated cross in May 2015 in a greenhouse in Enkhuizen, The Netherlands.

The first act of asexual reproduction of 'PEQZ0094' was accomplished when vegetative stem cuttings were propagated from the initial selection in June 2015 in a greenhouse in Enkhuizen, the Netherlands.

BRIEF SUMMARY OF INVENTION

Horticultural examination of plants grown from cuttings of the plant initiated in June 2015 in Enkhuizen, The Netherlands and continuing thereafter, has demonstrated that the combination of characteristics as herein disclosed for 'PEQZ0094' are firmly fixed and are retained through successive generations of asexual reproduction.

'PEQZ0094' has not been observed under all possible environmental conditions. The phenotype may vary significantly with variations in environment such as temperature, light intensity, and day length.

A Plant Breeder's Right for this cultivar has not yet been applied for. 'PEQZ0094' has not been made publicly available prior to the effective filing date of this application, notwithstanding any disclosure that may have been made less than one year prior to the effective filing date of this application by the inventor or another who obtained 'PEQZ0094' directly from the inventor.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

The accompanying photographic drawings show typical flower and foliage characteristics of 'PEQZ0094' with colors being as true as possible with an illustration of this type.

Figure 2:
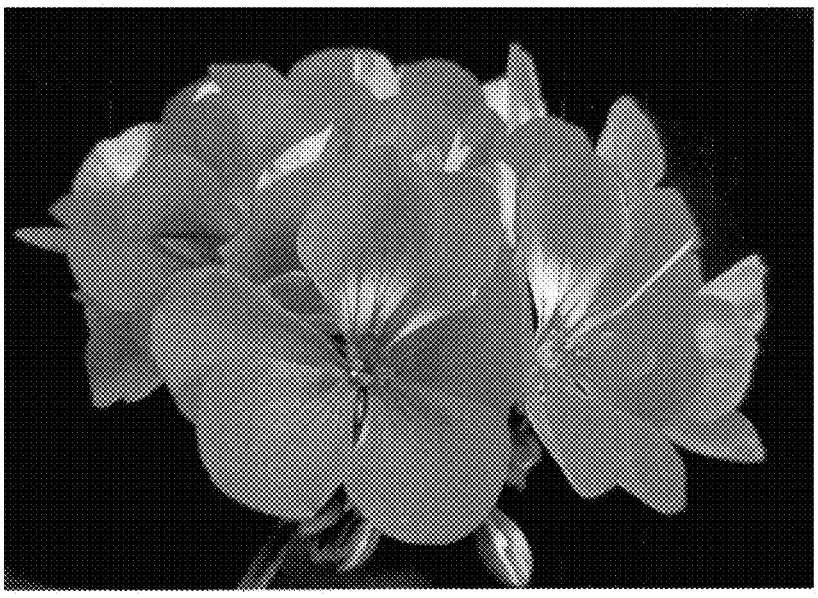

The photographic drawings show in FIG. 1, one flowering plant of the new variety and in FIG. 2, a close-up of an inflorescence.

DETAILED BOTANICAL DESCRIPTION

The plant descriptions and measurements were taken in Enkhuizen, The Netherlands in late June 2022 under natural light. These plants were approximately 18 weeks old and were grown in a 15 cm pots, in a greenhouse trial. The plant shown in the photograph was about 16 weeks old growing in a 12 cm pot in a greenhouse. The photographs were taken in May 2021.

Color references are made to The Royal Horticultural Society Colour Chart (R.H.S.) 2001.

TABLE 1

DIFFERENCES BETWEEN THE NEW VARIETY 'PEQZ0094' AND A MOST SIMILAR VARIETY

| | 'PEQZ0094' | 'PEQZ0009' (U.S. Plant Pat. No. 28,288) |
|---|---|---|
| Peduncle color: | Darkened grey purple RHS 187A | Green, RHS 137C |
| Stigma color: | Red-purple, RHS 61A | Light red, RHS 52C |

Plant:
- *Form, growth and habit.*—Upright, mounding habit.
- *Plant height.*—35-40 cm.
- *Plant height (inflorescence included).*—38-44 cm.
- *Plant width.*—35-42 cm.

Roots:
- *Number of days to initiate roots.*—15-18 days at about 22 degrees C.
- *Number of days to produce a rooted cutting.*—21-23 days at 22 degrees C.
- *Type.*—Fine, fibrous, free branching.
- *Color.*—RHS N155B but whiter.

Foliage:
- *Variegation.*—Absent.
- *Immature leaf, color upper surface.*—Closest to RHS 137C.
- *Immature leaf, lower surface.*—Closest to RHS 138B.
- *Mature leaf, color upper surface.*—Closest to RHS 139A.
- *Mature leaf, color lower surface.*—Closest to RHS 138A.
- *Length.*—8-10 cm.
- *Width.*—10-11 cm.
- *Shape.*—Cordate.
- *Base shape.*—Cordate.
- *Sinus of mature leaf.*—Wide.
- *Leaf base openness.*—Open.
- *Apex shape.*—Acute.
- *Margin.*—Slightly dentate.
- *Texture upper side.*—Hirsute.
- *Texture lower side.*—Hirsute.
- *Leaf zonation color.*—None.
- *Color of veins, upper surface.*—RHS 139A, largely indistinct.
- *Color of veins, lower surface.*—RHS 144B, becoming indistinct.
- *Pattern of veining.*—Palmate.
- *Petiole color.*—RHS 143B.
- *Petiole length.*—4.5-5 cm.
- *Diameter of petiole.*—0.35 cm.
- *Texture.*—Pilose, hirsute, glandular hairs.

Stem:
- *Quantity of branches.*—4-8.
- *Color of stem.*—Close to RHS 144A.
- *Anthocyanin coloration of stem.*—A weak anthocyanin coloration is visible.
- *Length of stem.*—9-17 cm.
- *Diameter.*—0.7 cm.
- *Length of internodes.*—2-4 cm.
- *Texture.*—Sparsely hirsute, pilose, glandular hairs.

Peduncle:
- *Color of peduncle.*—RHS 187A.
- *Length of peduncle.*—22-26 cm.
- *Peduncle diameter.*—0.4-0.5 cm.
- *Texture.*—Hirsute, glandular hairs.
- *Anthocyanin coloration of peduncle.*—Strong coloration.

Pedicel:
- *Color of pedicel.*—RHS 182B fading to RHS 187A at the tip.
- *Length of pedicel.*—3-3.5 cm.
- *Diameter of pedicel.*—0.15-0.2 cm.
- *Texture.*—Sparsely pilose, glandular hiars.
- *Pedicel swelling.*—Swelling was not observed.

Bud (just before opening):
- *Color.*—RHS N66B.
- *Length.*—1.2-1.4 cm.
- *Width.*—0.6-0.7 cm.
- *Shape.*—Elliptical.

Inflorescence:
- *Type.*—Umbel; semi-spherical or nearly semi-spherical.
- *Lastingness of individual flowers.*—7-9 days at 18° C. temperature.
- *Number of inflorescences per plant.*—6-12, with 5-12 immature umbels in various stages.
- *Average total number of buds.*—31-37.
- *Fragrance.*—None.
- *Umbel diameter.*—10-12 cm.
- *Umbel depth.*—8-9 cm.

Corolla:
- *Form.*—Semi-double.
- *Number of petals.*—6 with 1-3 petaloids.
- *Diameter of flower.*—4.5-5 cm.
- *Depth of flower.*—1.5-2 cm.
- *Side view shape.*—Concave.
- *Color upper petals, upper surface.*—Close to RHS N74B with a white base RHS N155A and veins RHS N178A.
- *Color upper petals, lower surface.*—In the center RHS N74D, fading to N74B towards the edges and veins RHS 67A.
- *Length of upper petals.*—2.5-2.7 cm.
- *Width of upper petals.*—1.7-1.9 cm.
- *Color lower petals, upper surface.*—RHS N74.
- *Color lower petals, lower surface.*—In the center RHS N74D, fading to RHS N74B towards the edges.
- *Markings on upper petals.*—White base RHS N155A and veins RHS N178A.
- *Markings on lower petals.*—None.
- *Length of lower petals.*—2.4-2.6 cm.
- *Width of lower petals.*—1.9-2.1 cm, petaloids variably smaller.
- *Petal shape.*—Obovate to spathulate.
- *Apex shape.*—Rounded.
- *Margin.*—Entire.
- *Base.*—Attenuate.
- *Petal texture.*—Papillose on both surfaces.

Calyx:
- *Number of sepals.*—5.
- *Color of sepals.*—RHS 138B, base RHS 182B.
- *Length of sepals.*—1-1.2 cm.
- *Width of sepals.*—0.2-0.4 cm.
- *Sepal shape.*—Lanceolate to linear.
- *Apex shape.*—Acute.

*Margins*.—Mostly fused.

*Texture, upper surface*.—Glabrous.

*Lower surface*.—Glandular hairs, hirsute.

*Sepal flexing*.—Mostly unflexed sepals. The narrowest sepals might flex moderately.

Reproductive organs:

Gynoecium:

*Pistil*.—RHS 61A at apex RHS 143A at the base.

*Length*.—0.8-0.9 cm.

*Style color*.—RHS 61A.

*Style length*.—0.4 cm.

*Stigma color*.—RHS 61A.

*Ovary color*.—RHS 143A.

*Ovary length*.—0.4-0.5 cm.

*Ovary diameter*.—0.2 cm.

Androecium:

*Number of stamens*.—6-9 with 1-5 staminoids.

*Color of filaments*.—Whiter than RHS N155A fading to RHS 63C at the apex.

*Length filaments*.—0.6-0.8 cm.

*Anther color*.—Close to RHS 63B.

*Length of anthers*.—0.3 cm.

*Color of pollen*.—RHS 185A.

*Pollen amount*.—Scarce.

*Fertility/seed set*.—Has not been determined to date.

*Disease/pest resistance*.—Has not been determined to date.

What is claimed is:

1. A new and distinct variety of *Pelargonium* plant named 'PEQZ0094' substantially as illustrated and described herein.

* * * * *